(12) United States Patent
Su

(10) Patent No.: US 7,923,240 B2
(45) Date of Patent: Apr. 12, 2011

(54) PHOTO-ACTIVATED FIELD EFFECT TRANSISTOR FOR BIOANALYTE DETECTION

(75) Inventor: Xing Su, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 496 days.

(21) Appl. No.: 11/394,156

(22) Filed: Mar. 31, 2006

(65) Prior Publication Data

US 2007/0231790 A1    Oct. 4, 2007

(51) Int. Cl.
 *C12M 1/34* (2006.01)
(52) U.S. Cl. .................................................. 435/287.2
(58) Field of Classification Search .................... 422/50, 422/82.1–82.3; 435/287.2
See application file for complete search history.

(56) References Cited

U.S. PATENT DOCUMENTS

| 5,106,751 | A  | * | 4/1992 | Newman | 435/287.1 |
| 6,180,415 | B1 | * | 1/2001 | Schultz et al. | 436/518 |
| 6,235,535 | B1 | * | 5/2001 | Keinanen et al. | 436/172 |
| 2002/0016008 | A1 | * | 2/2002 | Lockhart et al. | 436/518 |
| 2006/0197118 | A1 | * | 9/2006 | Migliorato et al. | 257/253 |
| 2009/0321261 | A1 | * | 12/2009 | Vlahovic et al. | 204/545 |

* cited by examiner

*Primary Examiner* — Ann Y Lam
(74) *Attorney, Agent, or Firm* — Pillsbury Winthrop Shaw Pittman LLP

(57) ABSTRACT

The application relates to a device and method for performing analyte detection, especially biomolecule detection. The device and method combine photo-induced charge separation in label materials and field effect transistors as sensors, resulting in more sensitive, specific and/or selective detections of biomolecules in multiplex assays, such as immunoassays and DNA microarray assays. The embodiments of the invention also encompass a device and method that comprise an array of electrical sensors, such as field effect transistors, and binding complexes for simultaneous multiplex detection of analytes.

47 Claims, 3 Drawing Sheets

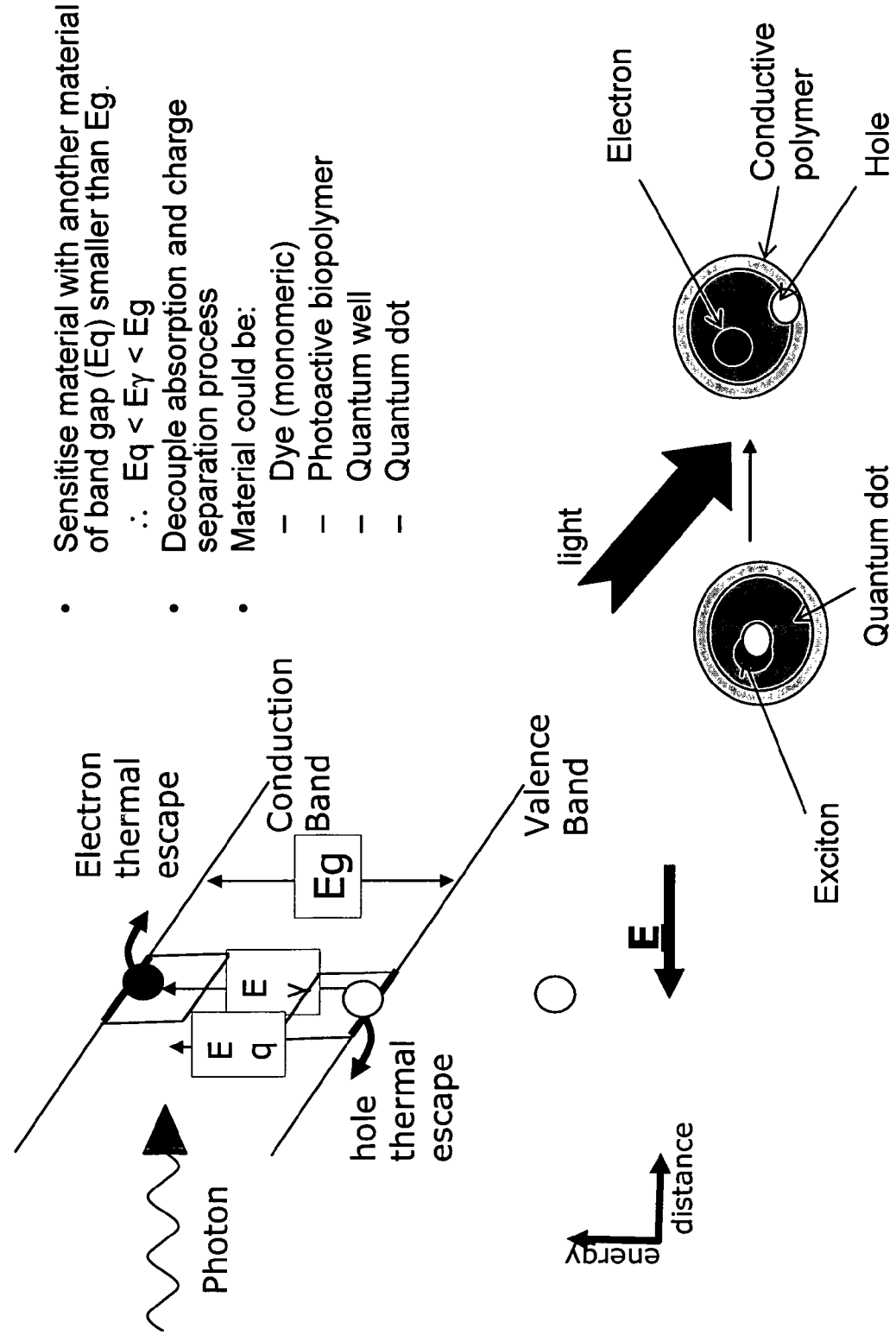
FIG. 1 Photoinduced Charge Separation

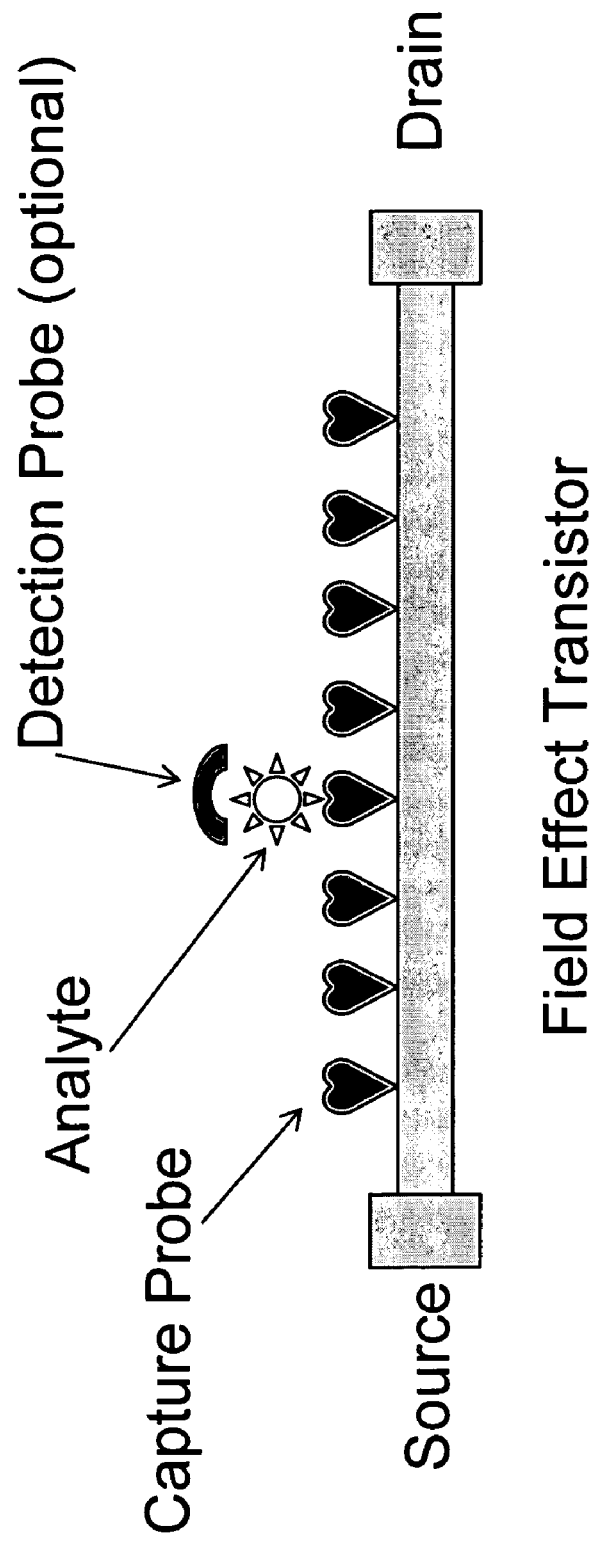
FIG. 2 Field Effect Transistors as Electrical Sensors

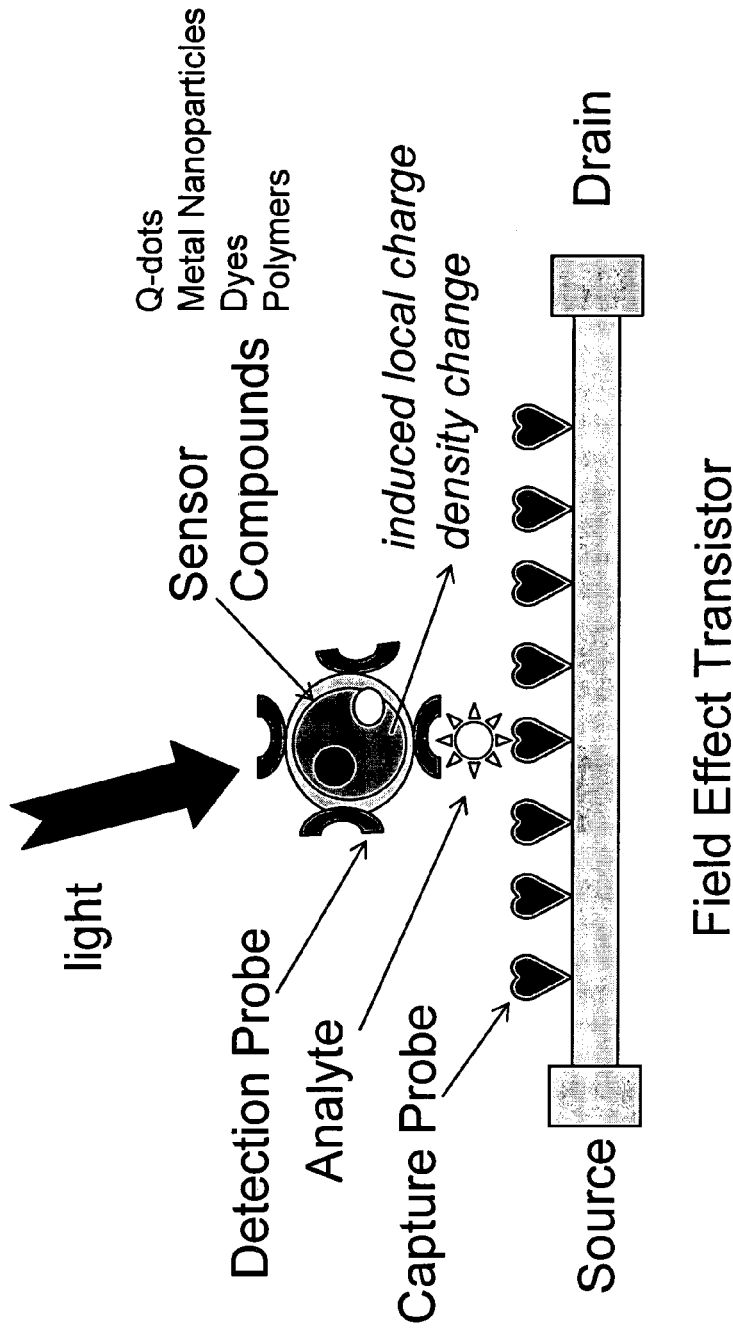

though the plotting of a standard curve on a graph, the position of the curve at response of the unknown is then examined, and so the quantity of the unknown found. The detection of the quantity

PHOTO-ACTIVATED FIELD EFFECT TRANSISTOR FOR BIOANALYTE DETECTION

RELATED APPLICATIONS

None.

FIELD OF INVENTION

The embodiments of the invention relate to a device and method for detection of analytes, especially, biomolecules. Specifically, the embodiments encompass using field effect transistors as electrical sensors in the detection of bioanalytes. The embodiments also encompass using photo-induced charge separation in connection with field effect transistors to achieve enhanced specificity and/or sensitivity in bioanalyte detection. The invention transcends several scientific disciplines such as, biochemistry, physics, microelectronics, immunology, molecular biology, and medical diagnostics.

BACKGROUND

Rapid and specific detections of biomolecules and biological cells, such as proteins, DNAs, and RNAs, viruses, peptides, antibodies, antigens, red blood cells, white blood cells, and platelets, have become more and more important to biological assays crucial to fields such as genomics, proteomics, diagnoses, and pathological studies. For example, the rapid and accurate detection of specific antigens and viruses is critical for combating pandemic diseases such as AIDS, flu, and other infectious diseases. Also, due to faster and more specific methods of separating and detecting cells and biomolecules, the molecular-level origins of disease are being elucidated at a rapid pace, potentially ushering in a new era of personalized medicine in which a specific course of therapy is developed for each patient. To fully exploit this expanding knowledge of disease phenotype, new methods for detecting multiple biomolecules (e.g., viruses, DNAs and proteins) simultaneously are increasingly desired and required. The multiplex biomolecule detection methods must be rapid, sensitive, highly parallel, and ideally capable of diagnosing cellular phenotype in vivo.

A specific type of biological assay increasingly used for medical diagnostics, as well as in food and environmental analysis, is immunoassay. An immunoassay is a biochemical test that measures the level of a substance in a biological liquid, such as serum or urine, using the reaction of an antibody its antigen. The assay takes advantage of the specific binding of an antibody to its antigen. Monoclonal antibodies are often used as they only usually bind to one site of a particular molecule, and therefore provide a more specific and accurate test, which is less easily confused by the presence of other molecules. The antibodies picked must have a high affinity for the antigen (if there is antigen available, a very high proportion of it must bind to the antibody). In an immunoassay, both the presence of antigen or antibodies can be measured. For instance, when detecting infection the presence of antibody against the pathogen is measured. For measuring hormones such as insulin, the insulin acts as the antigen.

Conventionally, for numerical results, the response of the fluid being measured must be compared to standards of a known concentration. This is usually done though the plotting of a standard curve on a graph, the position of the curve at response of the unknown is then examined, and so the quantity of the unknown found. The detection of the quantity present of antibody or antigen can be achieved by a variety of methods. One of the most common is to label either the antigen or antibody. The label may consist of an enzyme, radioisotopes, or a fluorophore.

A specific phenomenon that has been used in photo detection is photo-induced, or photo-activated, charge separation, which is the process of an electron in an atom being excited to a higher energy level and then leaving the atom to a nearby electron acceptor. Upon exposure to various radiation, electrons in many materials are capable of being excited and moved into another energy level. Specific materials suitable for photo-induced charge separation and for use in detection include dyes, photoactive polymers, quantum dots. Conventional detection devices involving photo-induced charge separation, however, usually are large in size and not suitable for inclusion in an integrated device.

An increasing amount of biological assays, such as immunoassays and gene sequencing, are being carried out on microarrays, such as DNA microarrays or protein microarrays. A microarray is a collection of microscopic spots, such as DNA or protein spots attached to a solid surface, such as glass, plastic or silicon chip forming an array. The microarrays can be used to measure the expression levels of large numbers of genes or proteins simultaneously. The biomolecules, such as DNAs or proteins, on microarray chip typically are detected through optical readout of fluorescent labels attached to a target molecule that is specifically attached or hybridized to a probe molecule. These optical methods are difficult to implement and miniaturize because they rely on the use of optical labels and require large or expensive instrumentation.

A field effect transistor (FET) is a transistor that relies on an electric field to control the conductivity of a channel in a semiconductor material. An FET has three terminals, which are known as the gate, drain and source. A voltage applied between the gate and source terminals modulates the current between the source and drain terminals. A small change in gate voltage can cause a large variation in the current from the source to the drain, thus enabling the FET to amplify signals.

FETs are commonly used for weak-signal amplification and can amplify analog or digital signals. They are also sometimes used as voltage-controlled resistors. Recently, FETs have been explored as sensors in chemical and biological detection. However, the detection sensitivity of current FETs is relatively low as compared to traditional photonic based detectors.

BRIEF DESCRIPTION OF THE DRAWINGS

FIG. 1 illustrates a photo-induced charge separation process.

FIG. 2 illustrates detection of an analyte using a field effect transistor as an electrical sensor.

FIG. 3 illustrates a photo-activated field effect transistor used for enhanced biomolecule detection.

DETAILED DESCRIPTION

Embodiments of the invention relate to a device and method that employ photo-induced charge separation and an electrical sensor detecting the charge separation. In the embodiments, the photo-induced charge separation is a reflection of specific chemical and/or biological interactions and is detected by the electrical sensors, which can be part of an integrated on-chip device for performing chemical analysis and medical diagnostics. In specific embodiments, the electrical sensor is a field effect transistor that detects photoinduced charge separations occur in materials involved in specific chemical or biological interactions.

The embodiments of the invention further relate to a device and method where an array of electrical sensors and corresponding molecular complexes are contained in a single substrate. Signals from the electrical sensor are detected and collected by circuitries on the substrate or in a separate device. One application of the electrical sensor array of the invention is their use in a protein or DNA array for simultaneous multiple protein or DNA analysis. The substrate of the embodiments of the invention may be part of an integrated device that also serves as a microarray or macroarray, an integrated circuit, a microfluidic device, a MEMS, or a combination. Therefore, samples contained or processed by the device may be also analyzed by the integrated device and the signals processed for analysis.

A biological sample often contains many thousands or even more types of biomolecules and clinical diagnosis needs to measure multiple analytes for disease confirmation. Currently, each analyte is measured separately, which requires multiple samples from a patient. The procedure is time consuming and labor intensive. Multiplex assays, in which multiple analytes can be measured at the same time, have been developed to solve this problem. However, in conventional multiplex assays, the detection of different types of labels, such as nanoparticles, are not effective due to signal strength and sensitivity.

Current photo detection devices are usually large in size and are difficult to be included in an integrated device. On the other hand, field effect transistors have the advantage of being small in size and easily integratable into a single device. But, due to problems related to signal intensity and sensitivity, FETs have drawbacks in serving as electrical sensors. Embodiments of the present invention combine the principles of photo-induced charge separation and field effect transistors as electrical sensors and achieve detection of analytes, especially bioanalytes, that is more specific and sensitive.

In the embodiments of the invention, analytes that can be detected include antigens of all types, such as proteins, polysaccharides, and small molecules coupled to a protein. The specific bindings between antigens and their corresponding antibodies form the basis of immunoassays. Antibodies suitable for the embodiments of the invention include monoclonal antibodies, polyclonal antibodies, recombinant antibodies, random peptides and aptamers. Immunoassays suitable for the embodiments of the invention include solid-phase immunoassays based the sandwich principle and the competing principle. Also included are specific types of immunoassays such as enzyme-linked immunosorbent assay (ELISA) and electrochemiluminescence (ECL).

Analytes in the embodiments of the invention also include nucleic acids (DNA and RNA), which can form double-stranded molecules by hybridization, that is, complementary base pairing. The specificity of nucleic acid hybridization is such that the detection of molecular and/or nanomaterials binding events can be done through electrical readout of polarization changes caused by the interaction of charged target molecules (DNA, RNA, proteins, for example.) and chemically modified nanomaterials (carbon nanotubes, nanowires, nanoparticles functionalized with DNA, for example) with complementary molecular probes (DNA, RNA, anti-body, for example) attached to the electrodes (such as Au, Pt, for example). This specificity of complementary base pairing also allows thousands of hybridization to be carried out simultaneously in the same experiment on a DNA chip (also called a DNA array).

Molecular probes or capture molecules are immobilized on the surface of individually addressable electrical sensor arrays through surface functionalization techniques. The arrays of the embodiments of the invention could be a DNA array (collections of DNA probes on a shared base) comprising a dense grid of spots (often called elements or pads) arranged on a miniature support. Each spot could represent a different gene.

The capture molecule or probe in a DNA chip is usually hybridized with a complex RNA or cDNA target generated by making DNA copies of a complex mixture of RNA molecules derived from a particular cell type (source). The composition of such a target reflects the level of individual RNA molecules in the source. The intensities of the signals resulting from the binding events from the DNA spots of the DNA chip after hybridization between the probe and the target represent the relative expression levels of the genes of the source.

The DNA chip could be used for differential gene expression between samples (e.g., healthy tissue versus diseased tissue) to search for various specific genes (e.g., connected with an infectious agent) or in gene polymorphism and expression analysis. Particularly, the DNA chip could be used to investigate expression of various genes connected with various diseases in order to find causes of these diseases and to enable accurate treatments.

Using embodiments of the invention, one could find a specific segment of a nucleic acid of a gene, i.e., find a site with a particular order of bases in the examined gene. This detection could be performed by using a diagnostic polynucleotide made up of short synthetically assembled single-chained complementary polynucleotide—a chain of bases organized in a mirror order to which the specific segment of the nucleic acid would attach (hybridize) via A-T or G-C bonds.

The practice of the embodiments of the invention may employ, unless otherwise indicated, conventional techniques of micro-electronics, nanotechnology, organic chemistry, polymer technology, molecular biology (including recombinant techniques), cell biology, biochemistry, and immunology, which are within the skill of the art. Such conventional techniques include polymer array synthesis, immunoassays, hybridization, ligation, detection of molecules, such as antibodies and hybridization using a label. Specific illustrations of suitable techniques can be had by reference to the example herein below. However, other equivalent conventional procedures can, of course, also be used.

As used in the specification and claims, the singular forms "a", "an" and "the" include plural references unless the context clearly dictates otherwise. For example, the term "an array" may include a plurality of arrays unless the context clearly dictates otherwise.

"Photo-induced charge separation" and "photo-activated charge separation" are used interchangeably and refer the phenomenon or process in which an electron in an atom is excited to a higher energy level and moves to another electron acceptor. Many materials are suitable for the phenomenon or process to occur. Specific materials include, but not limited to, organic and inorganic dyes, photoactive polymers, quantum dots, quantum wells, radio-active materials, magnetic materials, enzymes, liposome-based materials, chromophores, fluorophores, nanoparticles, composite-organic-inorganic nano-clusters, colloidal metal particles, or a combination thereof.

The term "photo-induced" or "photo-activated" generally refers to "radiation-induced" or "radiation-activated" and indicates that the related phenomenon or process is triggered or affected by the presence of radiation, which includes, but not limited to, electromagnetic radiation.

An "electrical sensor" refers to a substance or device that detects or senses an electrical signal created by movement of electrons, including but not limited to electrical resistance, current, voltage and power.

A "field effect transistor" or FET refers to a transistor that relies on an electric field to control the conductivity of a channel in a semiconductor material. An FET has three terminals, which are commonly known as the gate, drain and source. A voltage applied between the gate and source terminals modulates the current between the source and drain terminals. A small change in gate voltage can cause a large variation in the current from the source to the drain, thus enabling the FET to amplify signals.

An "array," "macroarray" or "microarray" is an intentionally created collection of substances, such as molecules, openings, microcoils, detectors and/or sensors, attached to or fabricated on a substrate or solid surface, such as glass, plastic, silicon chip or other material forming an array. The arrays can be used to measure the expression levels of large numbers, e.g., tens, thousands or millions, of reactions or combinations simultaneously. An array may also contain a small number of substances, e.g., a few or a dozen. The substances in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the pads on the array. A macroarray generally contains pad sizes of about 300 microns or larger and can be easily imaged by gel and blot scanners. A microarray would generally contain pad sizes of less than 300 microns.

"Substrate," "support" and "solid support" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "analyte," "target" or "target molecule" refers to a molecule of interest that is to be detected and/or analyzed, e.g., a nucleotide, an oligonucleotide, a polynucleotide, a peptide, or a protein. The analyte, target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The target molecule may be a fluorescently labeled antigen, antibody, DNA or RNA. A "bioanalyte" refers to an analyte that is a biomolecule.

The term "capture molecule" refers to a molecule that is immobilized on a surface. The capture molecule is generally, but not necessarily, binds to a target or target molecule. The capture molecule is typically an antibody, a nucleotide, an oligonucleotide, a polynucleotide, a peptide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. In the case of a solid-phase immunoassay, the capture molecule in immobilized on the surface of the substrate and is an antibody specific to the target, an antigen, to be detected. The capture molecule may be fluorescently labeled antibody, protein, DNA or RNA. The capture molecule may or may not be capable of binding to just the target molecule or just the probe molecule.

The term "probe" or "probe molecule" refers to a molecule that binds to a target molecule for the analysis of the target. The probe or probe molecule is generally, but not necessarily, has a known molecular structure or sequence. The probe or probe molecule may or may not be attached to the substrate of the array. The probe or probe molecule is typically an antibody, a nucleotide, an oligonucleotide, a polynucleotide, a peptide, or a protein, including, for example, monoclonal antibody, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) In immunoassays, the probe molecule may be a labeled antibody specific to the target, an antigen, to be analyzed. In such case, the capture molecule, the target molecule and the probe molecule form a "sandwich." The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

A "binding partner," refers to a molecule or aggregate that has binding affinity for one or more analytes, targets or other molecules. In this sense, a binding partner is either a "capture molecule" or a "probe molecule." Within the scope of the embodiments of the invention, virtually any molecule or aggregate that has a binding affinity for an analyte or target of interest may be a binding partner, including, but are not limited to, polyclonal antibodies, monoclonal antibodies, single-chain antibodies, chimeric antibodies, humanized antibodies, antibody fragments, oligonucleotides, polynucleotides, nucleic acids, aptamers, nucleic acid ligands and any other known ligand that can bind to at least one target molecule. Although, in certain embodiments a binding partner is specific for binding to a single target, in other embodiments the binding partner may bind to multiple targets that possess similar structures or binding domains.

"Binding" refers to an interaction between two or more substances, such as between a target and a capture or probe molecule, that results in a sufficiently stable complex so as to permit detection of the bound molecule complex. In certain embodiments of the invention, binding may also refer to an interaction between a second molecule and a target.

"Associated with" or "association" refers to a direct or indirect interactions between two or more substances, such as between a target and a capture or probe molecule, that results in a sufficiently stable complex. For example, a molecule or complex of molecules is "associated with" the surface of a substrate when the molecule or complex is either bound to the surface of the substrate directly, through another molecule or substance, or to both. In other words, substances are "associated with" each other when any one member of the substances is directly bound to at least another member of the substances. Additionally, a component of an integrated device is also "associated with" the device. For example, a transistor in an integrated circuit is "associated with" the circuit.

The terms "label," "tag" and "sensor compound" are used interchangeably to refer to a marker or indicator distinguishable by the observer but not necessarily by the system used to identify an analyte or target. A label may also achieve its effect by undergoing a pre-designed detectable process. Labels are often used in biological assays to be conjugated with, or attached to, an otherwise difficult to detect substance. At the same time, Labels usually do not change or affect the underlining assay process. A label or tag used in biological assays include, but not limited to, a radio-active material, a magnetic material, quantum dot, an enzyme, a liposome-based label, a chromophore, a fluorophore, a dye, a nanoparticle, a quantum dot or quantum well, a composite-organic-inorganic nano-cluster, a colloidal metal particle, or a combination thereof.

The terms "die," "polymer array chip," "array," "array chip," or "bio-chip" are used interchangeably and refer to a collection of a large number of capture molecules arranged on a shared substrate which could be a portion of a silicon wafer, a nylon strip or a glass slide. The term "DNA array" or "DNA array chip" is used when the array chip is used to analyze a nucleotide. The term "protein array" is used when the array chip is used to analyze a protein.

The term "chip" or "microchip" refers to a microelectronic device made of semiconductor material and having one or more integrated circuits or one or more devices. A "chip" or "microchip" is typically a section of a wafer and made by slicing the wafer. A "chip" or "microchip" may comprise many miniature transistors and other electronic components on a single thin rectangle of silicon, sapphire, germanium, silicon nitride, silicon germanium, or of any other semiconductor material. A microchip can contain dozens, hundreds, or millions of electronic components.

"Micro-Electro-Mechanical System (MEMS)" is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components could be fabricated using compatible "micromachining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms", to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, unprecedented levels of functionality, reliability, and sophistication can be placed on a small silicon chip at a relatively low cost.

"Microprocessor" is a processor on an integrated circuit (IC) chip. The processor may be one or more processor on one or more IC chip. The chip is typically a silicon chip with thousands of electronic components that serves as a central processing unit (CPU) of a computer or a computing device.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either $\alpha$-, $\beta$-, or $\omega$-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nanomaterial" as used herein refers to a structure, a device or a system having a dimension at the atomic, molecular or macromolecular levels, in the length scale of approximately 1-100 nanometer range. Preferably, a nanomaterial has properties and functions because of the size and can be manipulated and controlled on the atomic level.

The term "biomolecule" refers to any organic molecule that is part of a living organism. Biomolecules includes a nucleotide, a polynucleotide, an oligonucleotide, a peptide, a protein, a ligand, a receptor, among others. A "complex of a biomolecule" refers to a structure made up of two or more types of biomolecules. Examples of a complex of biomolecule include a cell or viral particles. A cell can include bacteria, fungi, animal mammalian cell, for example.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "polynucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers".

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogen atoms of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage or "sugar-phosphate backbone" of the polynucleotide can also be substituted or modified, for instance with methyl phosphonates, O-methyl phosphates or phosphorothioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

Nucleotides with modified bases can also be used in the embodiments of the invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the $N^2$ position with an imidazolyl propyl group, increasing duplex stability. Universal base analogues such as 3-nitropyrrole and 5-nitroindole can also be included. A variety of modified polynucleotides suitable for use in the embodiments of the invention are described in the literature.

When the macromolecule of interest is a peptide, the amino acids can be any amino acids, including α, β, or ω-amino acids. When the amino acids are α-amino acids, either the L-optical isomer or the D-optical isomer may be used. Additionally, unnatural amino acids, for example, β-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

A "fluorophore" or "fluorescent compound" can include, but is not limited to, a dye, intrinsically fluorescent protein, lanthanide phosphor, and the like. Dyes, for example, include rhodamine and derivatives, such as Texas Red, ROX (6-carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow, IAEDANS, 7-Me$_2$, N-coumarin-4-acetate, 7-OH-4-CH$_3$-coumarin-3-acetate, 7-NH$_2$-4CH$_3$-coumarin-3-acetate (AMCA), monobromobimane, pyrene trisulfonates, such as Cascade Blue, and monobromotrimethyl-ammoniobimane.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

One embodiment of the invention relates to a device for detection of analytes. The device comprises an electrical sensor and a complex associated with a surface of the electrical sensor. According to the embodiment, the complex comprises a label capable of creating an electrical charge change upon being exposed to radiation and the electrical sensor is capable of detecting the electrical charge change.

The embodiment of the invention, therefore, encompasses a complex that comprises a label capable of creating a radiation induced electrical charge separation and an electrical sensor capable of detecting, and/or used to detect, the charge separation. The embodiment further specifies that the complex comprising the label be associated with a surface of the electrical sensor, which is capable of detecting the electrical charge separation.

According to an embodiment of the invention, any sensor capable of detecting an electrical charge separation can be used as the electrical sensor. To this effect, the sensor should have a surface that facilitates that association of the sensor with the complex, especially in such a way that a charge separation created by the label comprised in the complex is detectable by the electrical sensor. Specifically, the electrical sensor comprises an exposed electrode surface for the detection of, or to detect, electrical impedance, current or voltage.

In a specific embodiment, the electrical sensor comprises an electromagnetic sensor, a transistor, an electrical resistance sensor, an electrical power sensor, a magnetism sensor, an electrical voltage sensor, or an electrical current sensor. Specific detection systems can be used as part or all of the electrical sensor include an ohmmeter, a multimeter, a galvanometer, an ammeter, a leaf electroscope, a voltmeter, a watt-hour meter, a magnetic compass, a fluxgate compass, or a magnetometer.

In another embodiment, the electrical sensor is a field effect transistor (FET). As discussed herein, an FET is a transistor that relies on an electric field to control the conductivity of a "channel" in a semiconductor material. An FET usually has three terminals, which are known as the gate, drain and source. A voltage applied between the gate and source terminals modulates the current between the source and drain terminals. In other words, In an FET, electrical current flows along a semiconductor path called the channel. At one end of the channel, there is an electrode called the source. At the other end of the channel, there is an electrode called the drain. Although the physical diameter of the channel is fixed for a given FET, its effective electrical diameter can be varied by the application of a voltage to a control electrode called the gate.

According to the embodiment, the complex comprising the label is associated with a surface on or near the gate area of the transistor such that an electrical charge separation created within the label will create a voltage between the gate and source of the FET, thus creating an electrical current between the source and the drain of the FET. As discussed herein, both the mode of operation of the FET and strength of the current can be measured so that both the existence and strength of the electrical charge separation are detected.

Many types of field effect transistor can be used in the embodiments of the invention, including both junction FET (JFET) and metal-oxide-semiconductor FET (MOSFET), as well as both the N-type semiconductor (N-channel) or P-type semiconductor (P-channel). In a specific embodiment, the FET is an MOSFET), a JFET, a metal-semiconductor FET (MESFET), or a high-electron-mobility (HEMFET).

In another embodiment of the invention, various nanomaterials can be used in the field effect transistor, especially for serving as the channel between the source and drain, for enhanced sensitivity and selectivity. In a specific embodiment, the FET comprises a nanowire, a nanocrystal, or a nanotube, such as a single-walled or multi-walled carbon nanotube. The FET may also comprise a nanopillar, a nanogap, a patterned nanostructure.

According to another embodiment of the invention, the surface area of the FET is functionalized. The functionalization enables the FET to be responsive to more variety of and specific analyte species, more sensitive, more selective, and/or protective against non-specific bindings. The functionalization can be obtained through various methods and materials. For example, the surface area of the FET can be coated by various polymers, including polyethylene-imine (PEI), triblock copolymer chains, and poly (sodium 4-styrene-sulfonate), Nafion, and buffers such as Tween 20. People skilled in the art should know the best ways to functionalize the surface of a specific FET depending on the type of FET, the material used for the channel and surface area, and the type of detection to be carried out.

In one embodiment of the invention, the complex associated with a surface of the electrical sensor comprises a first binding partner immobilized on the surface of the sensor and an analyte bound to the first binding partner. According to this embodiment, the label is bound to the analyte. In another embodiment, the complex comprises a first binding partner immobilized on the surface of the electrical sensor, an analyte bound to the first binding partner, and a second binding partner bound to the analyte. According to this embodiment, the label is bound to the second binding partner.

In the above embodiments of the invention, the first binding partner is immobilized on a surface of the sensor. The immobilization may be permanent or reversible. Further, the immobilization can be made by forming a covalent bond between the first binding partner and the surface or any functional group on the surface, or by other chemical/physical mechanisms. The binding of the first binding partner to the surface facilitates the association of the complex with the surface. As discussed herein, the complex is "associated with" the surface of the electrical sensor when any member of the complex is bound to the surface of the substrate directly. In the embodiments of the invention, the complex comprises one or more of a first binding partner that is immobilized on the surface of the substrate, an analyte that is bound to the first binding partner, a second binding partner that is bound to the analyte and a label that is bound to the analyte or the second binding partner. Under this circumstance, the label, the second binding partner and the analytes are also "associated with" the surface of the substrate. In the embodiments, the analyte, the second binding partner and the label may or may not be bound to the surface of the substrate directly. Further, the label may or may not be bound to the first and second binding partner and analyte directly.

In the embodiments of the invention, the analyte encompasses any compound, molecule or aggregate of interest for detection or analysis. Non-limiting examples of the analyte include an antibody, protein, peptide, receptor, antigen, DNA, RNA, polynucleotide, nucleic acid, carbohydrate, lipid, bacterium, macromolecule, allergen, carbohydrate, polysaccharide, glycoprotein, growth factor, cytokine, lipid, hormone, metabolite, cofactor, inhibitor, drug, pharmaceutical, poison, explosive, pesticide, nutrient, toxin, chemical warfare agent, biowarfare agent, biohazardous agent, infectious agent, prion, radioisotope, vitamin, carcinogen, mutagen, narcotic, heterocyclic aromatic compound, amphetamine, barbiturate, hallucinogen, waste product, and contaminant.

In one embodiment of the invention, the analyte comprises a biomolecule. More specifically, the analyte comprises an antigen, antibody, protein, peptide, virus, DNA, RNA, polynucleotide, nucleic acid, carbohydrate, lipid, bacterium, or macromolecule.

In the embodiments of the invention, the first binding partner or the second binding partner comprises, independently an antibody, such as a polyclonal antibody, monoclonal antibody, single-chain antibody, chimeric antibody, humanized antibody, antibody fragments, an antigen, a oligonucleotide, a polynucleotide, a nucleic acids, an aptamer, a nucleic acid ligand and any other known ligand that can bind to at least one target molecule In one embodiment of the invention, the analyte comprises an antigen and the first and second binding partners independently comprise an antibody to the antigen. The embodiment encompasses part of all of a sandwich type immunoassay, such as an ELISA type of detection assay, in which the first binding partner, or the capture molecule, is an antibody with affinity for the analyte, usually an antigen. After binding of the analyte to first binding partner, a second molecule, the second binding partner or probe molecule, which is typically a tagged antibody with an affinity for a different epitope of the analyte, is added and the complex of first binding partner/analyte/second binding partner with label is detected. In alternative embodiments, the first binding partner may have affinity for an analyte while the second binding partner has affinity for the first binding partner. Although detection may involve the use of a tagged second binding partner with affinity for the analyte, in alternative embodiments the first binding partner or the analyte may also be tagged for detection. The skilled artisan will be familiar with a variety of techniques by which an analyte/binding partner complex may be detected, any of which may be utilized within the scope of the embodiments of the invention.

In another embodiment of the invention, the analyte comprises a polynucleotide, such as a DNA or RNA, and the first and second binding partners independently comprise a complementary polynucleotide. The embodiment encompasses part or all of a sandwich type hybridization assay, in which the first binding partner, or the capture molecule/sequence, is a polynucleotide complementary to the analyte polynucleotide, usually a DNA sequence. After binding of the analyte to the first binding partner, a second molecule, the second binding partner or probe molecule/sequence, which is typically a tagged DNA sequence, is added and the complex of first binding partner/analyte/second binding partner with label is detected. In alternative embodiments, the first binding partner may have affinity for an analyte while the second binding partner has affinity for the first binding partner. Although detection may involve the use of a tagged second binding partner with affinity for the analyte, in alternative embodiments the first binding partner or the analyte may also be tagged for detection. The skilled artisan will be familiar with a variety of techniques by which an analyte/binding partner complex may be detected, any of which may be utilized within the scope of the embodiments of the invention.

In the embodiments of the invention, the label, or sensor compound, includes any material that, upon exposure to radiation, is capable of undergoing an electrical charge. In a specific embodiment, the label comprises a dye, a photoactive polymer, quantum dot, a quantum well, a fluorophore, a nanoparticle, a composite-organic-inorganic nano-cluster, a colloidal metal, a radio-active material, a magnetic material, an enzyme, a liposome-based label, a chromophore, or a combination thereof. According to another embodiment, quantum dots, quantum wells, monomeric or polymeric dyes, or photoactive biopolymers are materials especially suitable for serving as the label. Thus, according to the embodiments of the invention, even though the label itself may or may not be detectable directly, it is capable of undergoing a detectable process, i.e., electrical charge change, which is detectable.

In the embodiments of the invention, an electrical charge change includes an electrical perturbation, impedance, current, voltage, or a photo-induced charge separation caused by the electrical charge change. Specifically, an electrical charge change includes a photo-induced, or radiation-induced, charge separation and a local electrical perturbance, e.g., surrounding one or more nanoparticles. The perturbance may be sensible by an electrical sensor in the forms of current, potential, impedance, or field effect.

In this regard, the embodiments of the invention can enable real-time detection of electrical charge changes caused by molecular binding events, such as biomolecular interactions discussed herein. In certain embodiments of the invention, the detection of an electrical perturbation, impedance, current, voltage, or a photo-induced charge separation by an FET is distance dependent. Specifically, when distance between the charge separation and the surface of the FET is in the nanometer (nm) range, the sensitivity of the detection is dependent upon the distance. In certain circumstances, complex far away from the surface may not be detected. Thus, in a specific embodiment of the invention, the distance between the complex and the surface is less than 1000 nanometer (nm). In another embodiment, the association of complex and the surface of the electrical is such that the detection of electrical charge change of the complex by the electrical sensor is distance dependent.

According to the embodiments of the invention, radiation can be magnetic field, radio frequency, microwave, terahertz radiation, infrared, light. In this regard, the radiation can be electromagnetic radiation, gamma radiation, gravitational radiation, particle radiation, alpha radiation, beta radiation, or neutron radiation. In a specific embodiment, the radiation is electromagnetic radiation in the form of electrical energy, radio, microwave, infrared, visible light, ultraviolet light, X-rays, or gamma rays. According to the embodiment, the radiation should not affect the underlying chemical or biological binding process, but only create an electrical charge separation within the label used in the process. A person skilled in the art should know the type and strength of the radiation to be used for the detection based on the nature of the electrical sensor and it surface, the biding partners, the analytes and the labels used in the procedure.

FIGS. 1-3 illustrate specific embodiments of the invention. As shown in FIG. 1, photo-induced charge separation can be achieved by sensitizing a material with another material of band gap (Eq) smaller than Eg. Therefore, Eq<Eγ<Eg. As shown, the photon absorption process is decoupled from the charge separation process. Materials that can be used in the process include semiconductor materials, such as quantum wells and quantum dots; and materials such as monomeric dyes, photoactive biopolymers can be ionized upon radiation, leading to local charge changes. Metal nanoparticles can generate surface plasmon when receiving light radiation especially in resonance; and resonant surface plasmon can also create changes in local electrical field. In addition, nanoparticles can be used to sense radio frequency to generate local heating effect. The heating effect can create local charge perturbance, which can then be sensed by electrical device.

FIG. 2 illustrates a field effect transistor as an electrical sensor for molecular detection. As shown, capture molecules or capture probes, such as antibodies, are immobilized on a surface of the gate area of a field effect transistor. An analyte, such as an antigen of the antibody, is bound to the antibody. This binding event may be detected by the transistor if the binding creates an electrical charge change. Optionally, a detection probe or probe molecule, such as another antibody to the antigen, may be bound to the analyte. Similarly, the binding event may be detected by the transistor if the binding creates an electrical charge change. As discussed herein, the binding of the capture molecule/analyte/probe molecule may not create an electrical signal strong or sensitive enough to be accurately or consistently detected by the field effect transistor.

FIG. 3 illustrates an embodiment of the invention, in which a photo-activated field effect transistor (PAFET) is used to enhanced biomolecule detection sensitivity. As shown, capture molecules or capture probes, such as antibodies, are immobilized on a surface of the gate area of a field effect transistor. An analyte, such as an antigen of the antibody, is bound to the antibody. A detection probe or probe molecule, such as another antibody to the antigen, is then bound to the analyte. In the embodiment, the detection probe is conjugated with a sensor compound, or label, which may comprise quantum dots, a metal nanoparticles, dyes or polymers. The binding complex is then exposed to light, which may be in any of many forms of radiation, such that a local charge density change is induced. The transistor is turned on due to the charge density change.

In the embodiment of the invention as shown in FIG. 3, the specific binding between and analyte and the capture and detection probes takes place on or near the surface of the gate area of the field effect transistor. Further, the sensor compound, or label, is conjugated with the detection probe, or optionally with the analyte, the sensor compound too is on or near the surface. Thus, when binding complex is exposed to light, the electrical charge density change also takes place on or near the surface of the gate area of the transistor, which produces stronger, more sensitive and consistent signals detectable by the transistor.

According to another embodiment of the invention, the device or the electrical sensor is part of another device, e.g., an integrated circuit. Thus, in one embodiment, the electrical sensor is associated with a substrate, which may comprise a polymer, silicon or glass. In another embodiment, the substrate comprises a microarray, a macroarray, a multi-well plate, a microfluidic device, an integrated circuit, a MEMS or a combination thereof. The substrate may further comprise a microprocessor capable of processing signals or data detected by the electrical sensor.

In the embodiment of the invention, specific materials useful as the substrate include, but not limited to, polystyrene, polydimethylsiloxane (PDMS), silicon, glass, chemically functionalized glass, polymer-coated glass, nitrocellulose coated glass, uncoated glass, quartz, natural hydrogel, synthetic hydrogel, plastics, metals, and ceramics. The substrate may comprise any platform or device currently used for carrying out immunoassays, DNA or protein microarray analysis. Thus, the substrate may comprise a microarray or a macroarray, a multi-well plate, a microfluidic device, an integrated circuit, MEMS, or a combination thereof. Furthermore, the substrate may not be flat, and may comprise beads, particles, or other shaped objects.

In another embodiment of the invention, the substrate comprises a microprocessor comprising software or a hardware to process signal or data from the device or the electrical sensor.

For example, the phase/intensity information as electrical signals generated by the sensor may be read to the microprocessor to transform and generate data, such as the type and quantity of a specific analyte detected.

In another embodiment of the invention, the substrate comprises a platform or device on which a chemical or biological assay is being performed. Specifically, the substrate may comprise a device for performing an immunoassay, such as an ELISA assay, wherein a sandwich type binding of antibody/antigen/antibody has been formed. The substrate may also comprise a DNA microarray assay, wherein a sandwich type capture molecule/target DNA/probe molecule binding has been formed. Thus, the device and detection according to the embodiments of the invention may be part of a larger device or process in which sequential and multiplex procedures may be performed.

In the embodiments of the invention, the microfluidic channel or multiple microfluidic channels may be part of the substrate, which may be an integrated device, such as an integrated circuit, a microfluidic device, or a MEMS. The microfluidic channels or their integrated devices can be made by using techniques known to skilled artisans or methods disclosed herein. For example, the microfluidic channels may be made by soft lithography method with poly-dimethyl siloxane. With these techniques it is possible to generate patterns with critical dimensions as small as 30 nm. These techniques use transparent, elastomeric polydimethylsiloxane (PDMS) "stamps" with patterned relief on the surface to generate features. The stamps can be prepared by casting pre-polymers against masters patterned by conventional lithographic techniques, as well as against other masters of interest. Several different techniques are known collectively as soft lithography. They are as described below:

Near-Field Phase Shift Lithography. A transparent PDMS phase mask with relief on its surface is placed in conformal contact with a layer of photoresist. Light passing through the stamp is modulated in the near-field. If the relief on the surface of the stamp shifts the phase of light by an odd multiple of a predetermined number, a node in the intensity is produced. Features with dimensions between 40 and 100 nm are produced in photoresist at each phase edge.

Replica Molding. A PDMS stamp is cast against a conventionally patterned master. Polyurethane is then molded against the secondary PDMS master. In this way, multiple copies can be made without damaging the original master. The technique can replicate features as small as 30 nm.

Micromolding in Capillaries (MIMIC). Continuous channels are formed when a PDMS stamp is brought into conformal contact with a solid substrate. Capillary action fills the channels with a polymer precursor. The polymer is cured and the stamp is removed. MIMIC is able to generate features down to 1 μm in size.

Microtransfer Molding ((TM). A PDMS stamp is filled with a prepolymer or ceramic precursor and placed on a substrate. The material is cured and the stamp is removed. The technique generates features as small as 250 nm and is able to generate multilayer systems.

Solvent-assisted Microcontact Molding (SAMIM). A small amount of solvent is spread on a patterned PDMS stamp and the stamp is placed on a polymer, such as photoresist. The solvent swells the polymer and causes it to expand to fill the surface relief of the stamp. Features as small as 60 nm have been produced.

Microcontact Printing ((CP). An "ink" of alkanethiols is spread on a patterned PDMS stamp. The stamp is then brought into contact with the substrate, which can range from coinage metals to oxide layers. The thiol ink is transferred to the substrate where it forms a self-assembled monolayer that can act as a resist against etching. Features as small as 300 nm have been made in this way.

Techniques used also include micromachining of silicon for microelectricalmechanical systems (MEMS), and embossing of thermoplastic with patterned quartz. Unlike conventional lithography, these techniques are able to generate features on both curved and reflective substrates and rapidly pattern large areas. A variety of materials could be patterned using the above techniques, including metals and polymers. The methods complement and extend existing nanolithographic techniques and provide new routes to high-quality patterns and structures with feature sizes of about 30 nm.

Standard lithography on silicone wafer or silica glass could also be used to fabricate the devices of the embodiments of this invention. Chambers or channels can be made from the devices, fluidic flow can be controlled by pressure gradient, electrical field gradient, gravity, heat gradient etc. The labels or label-conjugated molecules can also be separated by planar device with a single a plurality of chambers, where the surfaces are modified with polymers (polyethylene glycol (PEG)-dramatized compounds) that can minimize non-specific binding.

Embodiments of the present invention also encompass a device for analyte detection that comprises an array of electrical sensors and the associated complexes. Specifically, the device comprises an array of electrical sensors and a complex associated with a surface of each of at least a portion of the electrical sensors. In the embodiment, the complex comprises a label capable of creating an electrical charge change upon being exposed to radiation and the associated electrical sensor is capable of detecting the electrical charge change.

Thus, according to the embodiment, the device comprises an array of electrical sensors, such as field effect transistors, in a pre-designed pattern. In a specific embodiment, at least a portion of the electrical sensors are individually addressable. In other words, the type, location and electrical connection of the individual sensors are determined and controlled as desired. The embodiment enables the simultaneous and multiplex detection and analysis of analytes.

In one embodiment, each of at each of at least a portion of the electrical sensors is associated with one or more complexes. In other words, any individual sensor in the array of sensors may be associated with multiple or a single complex, according to the specific analytes involved and detections to be carried out. For example, one embodiment may be that each of at least a portion of the electrical sensors of the device is associated with a single complex.

In another embodiment, a single complex is associated with two or more electrical sensors. For example, when the dimension or size of the complex is in the range of micrometers (μm) and the dimension or size of the electrical sensor is in the range μm or nanometers (nm), a single complex may be associated with a plurality of electrical sensors. In such a case, the individual sensors are more closely associated with specific regions of the complex. The sensors, each individually addressable, can work together in a coordinated manner to reflect a more accurate change in electrical charges of the complex.

In a specific embodiment, the complexes associated with a single electrical sensor comprise the same analyte. In another embodiment, at least two of the complexes associated with a single electrical sensor comprise different analytes. Similarly, the complexes associated with at least two of the electrical sensors may comprise the same or different analyte. It can be seen, therefore, embodiments of the invention allow flexible designs of the device, the arrays of electrical sensors and the complexes. A person skilled in the art should be able to design suitable devices for specific analysis according to disclosures made herein.

Another embodiment of the invention relates to a method of detecting an analyte. The method comprises: (1) providing an electrical sensor having a surface; (2) associating a complex with the surface, in which the complex comprises the analyte and a label capable of creating an electrical charge change upon being exposed to radiation; (3) radiating the complex; and (4) detecting the electrical charge change using the electrical sensor.

In one embodiment, the electrical sensor is a field effect transistor (FET). More specifically, the FET comprises a nanowire, a nanocrystal, or a nanotube, such as a single-walled carbon nanotube. The FET may also comprises a nanopillar, a nanogap, or a patterned nanostructure.

In another embodiment, the method further comprises functionalizing the surface of the electrical sensor. Specifically, the functionalizing comprises coating a polymeric material on the surface of the electrical sensor. For example, the functionalization may be carried out using layer by layer deposition of polymers, self-assembled monolayer (SAM), or providing functional groups, such as carboxyl, amine, or —HS.

The embodiments of the invention encompass a sandwich type immunoassay or DNA microarray assay. In such assays, a first binding partner, such as an antibody or capture DNA molecule is first immobilized on the surface of the substrate, e.g., a glass slide or microarray. The analyte, such as an antigen or target DNA molecule, is then bound to the first binding partner. A second binding partner, such as an antibody or probe DNA molecule, conjugated with, or attached to a sensor compound, is bound to the analyte. Optionally, the sensor compound may be conjugated with the analyte directly, without the involvement of a second binding partner. The complex of first binding partner/analyte/second binding partner/label, or optionally, first binding partner/analyte/label, is now associated with the surface of the substrate. In the embodiment of the invention, the analyte may or may not be bound to the surface of the substrate. The second binding partner may or may not be bound to the surface of the substrate or the first binding partner and that the label may or may be bound to the analyte, the first binding partner or the surface of the substrate.

In one embodiment of the invention, the associating of the complex with the surface of the electrical sensor comprises: (1) immobilizing a first binding partner on the surface; and (2) binding the analyte with the first binding partner, the analyte being conjugated with the label. In this embodiment, the label, or sensor compound, is conjugated with the analyte. Therefore, a second binding partner, such as a probe molecule, is not necessary.

In another embodiment, the associating of the complex with the surface of the electrical sensor comprises: (1) immobilizing a first binding partner on the surface; (2) binding the analyte with the first binding partner; and (3) binding a second binding partner with the analyte, the second binding partner being conjugated with the label. In this embodiment, the label is conjugated with the second binding partner, as in a traditional sandwich type immunoassay.

In the embodiments of the invention, the immobilization of the first binding partner on the surface of the electrical sensor can be carried out in many different chemical and/or electrical means. For example, by non-covalent means, such as adsorption, by covalent means, such as crosslinking, by using chemical mediators, by photo activation, and by in situ synthesis using photo masks. Specific manners used for specific biding partners will depend on the nature of the binding partner, the surface and other substances involved in the process.

In one embodiment of the invention, the immobilization of the first binding partner to the surface of the electrical sensor comprises contacting the surface with a buffer comprising the first binding partner, incubating the buffer, and washing the surface. Any suitable buffer may be used for the immobilization. The temperature and duration of the incubation process will be determined according to the nature of the surface, the first binding partner, and the subsequent binding events. Also, the first binding partner may be immobilized in a predetermined pattern to form a desired array. The washing step helps to remove any non-binding substance and prepare the surface for the subsequent procedures.

In a specific embodiment, after the immobilization of the first binding partner, a buffer containing a blocking agent is applied over the surface of the sensor. The buffer is then incubated and the surface is washed. The blocking agent helps to block non-specific binding spots on the surface of the substrate, such that the specific binding abilities of the first binding partner are expressed more prominently. Any suitable blocking agent, such as albumin, may be used for the embodiment.

In another embodiment of the invention, the binding of the analyte, or label conjugated analyte, with the first binding partner comprises contacting the surface of the sensor with a buffer comprising the analyte, incubating the buffer, and washing the surface. In the embodiment, any suitable buffer may be used for the binding event. The temperature and duration of the incubation process will be determined according to the nature of the surface, the analyte, the first binding partner used, and the subsequent binding events. A skilled artisan would know how to achieve the desired binding effect according to the materials used under the specific situation. The washing step helps to remove any non-binding substance and prepare the surface for the subsequent procedures.

In another embodiment of the invention, the binding of the label-conjugated second binding partner with the analyte comprises contacting the surface of the sensor with a buffer comprising the label-conjugated second binding partner, incubating the buffer, and washing the surface. In the embodiment, the second binding partner is pre-conjugated with a suitable label. Again, any suitable buffer may be used for the binding event. The temperature and duration of the incubation process will be determined according to the analyte, the binding partner and label used and the subsequent binding events. A skilled artisan would know how to achieve the desired binding effect according to the materials used under the specific situation. The washing step helps to remove any non-binding substance and prepare the surface for the subsequent procedures.

In the embodiments of the invention, once the first binding partner is immobilized on the surface of the substrate and the complex of first binding partner/analyte/second binding partner/label is associated with the surface of the substrate, the label is disassociated, or detached or removed, from the surface. As discussed herein, in conventional assays, such as solid-phase immunoassay and DNA microarray assays, the detection is performed by photo detectors when the binding events are complete. Also, the electrical sensor may also serve as the detector to detect electrical signals produced by the binding events. Embodiments of the present invention provide a novel method for detecting the analytes, in which the binding complex is exposed to radiation that produces an electrical charge change such as a charge separation with the label. The charge change is then detected by the electrical sensor, with enhanced signal, sensitivity and/or selectivity.

In one embodiment of the invention, the radiating can be by means of electromagnetic radiation, gamma radiation, gravitational radiation, particle radiation, alpha radiation, beta radiation, or neutron radiation. In a specific embodiment, the radiation is electromagnetic radiation in the form of electrical energy, radio, microwave, infrared, visible light, ultraviolet light, X-rays, or gamma rays. According to the embodiment, the radiation should not affect the underlying chemical or biological binding process, but only create an electrical charge separation within the label used in the process. A person skilled in the art should know the type and strength of the radiation to be used for the detection based on the nature of the electrical sensor and it surface, the biding partners, the analytes and the labels used in the procedure.

In another embodiment, detecting an electrical charge change includes detecting an electrical perturbation, impedance, current, voltage, or a photo-induced charge separation caused by the electrical charge change. Specifically, an electrical charge change includes a photo-induced, or radiation-induced, charge separation and a local electrical perturbance, e.g., surrounding one or more nanoparticles. The perturbance may be sensible by an electrical sensor in the forms of current, potential, impedance, or field effect. In one embodiment, the detecting is by means of measuring electrical current caused by the electrical charge change. More specifically, when the electrical sensor is a field effect transistor, the detecting is by means of measuring electrical current between the source and drain of the FET.

In this regard, the embodiments of the invention encompass real-time detection of electrical charge changes caused by molecular binding events, such as biomolecular interactions discussed herein. Therefore, the embodiments of the invention enable detection of bioanalytes without certain required steps associated with traditional sandwich type immunoassay, such as washing/rinsing after certain biding events. In certain embodiments of the invention, the detection of an electrical perturbation, impedance, current, voltage, or a photo-induced charge separation by an FET is distance dependent. Specifically, when distance between the charge separation and the surface of the FET is in the nanometer (nm) range, the sensitivity of the detection is dependent upon the distance. In certain circumstances, complex far away from the surface may not be detected.

Binding kinetics (initial rate etc) or static value can be used. The detection may further comprise processing signals or data detected by the electrical sensor.

Another embodiment of the invention relates to a method of detecting an analyte. The method comprises: (1) providing an array of electrical sensors; (2) associating a complex with a surface of each of at least a portion of the sensors, in which the complex comprises the analyte and a label capable of creating an electrical charge change upon being exposed to radiation; (3) radiating the surface; and (3) detecting the electrical charge change using at least a portion of the electrical sensor.

Thus, according to the embodiment, the method comprises simultaneous detections of multiple analytes using an array of electrical sensors, such as field effect transistors; in a pre-designed pattern. In a specific embodiment, at least a portion of the electrical sensors are individually addressable. In other words, the type, location and electrical connection of the individual sensors are determined and controlled as desired. The embodiment enables the simultaneous and multiplex detection and analysis of analytes.

In one embodiment of the method, each of at each of at least a portion of the electrical sensors is associated with one or more complexes. In other words, any individual sensor in the array of sensors may be associated with multiple or a single complex, according to the specific analytes involved and detections to be carried out. For example, one embodiment may be that each of at least a portion of the electrical sensors of the device is associated with a single complex.

In a specific embodiment, the complexes associated with a single electrical sensor comprise the same analyte. In another embodiment, at least two of the complexes associated with a single electrical sensor comprise different analytes. Similarly, the complexes associated with at least two of the electrical sensors may comprise the same or different analyte. It can be seen, therefore, embodiments of the invention allow flexible designs of the device, the arrays of electrical sensors and the complexes. A person skilled in the art should be able to design suitable devices for specific analysis according to disclosures made herein.

This application discloses several numerical range limitations that support any range within the disclosed numerical ranges even though a precise range limitation is not stated verbatim in the specification because the embodiments of the invention could be practiced throughout the disclosed numerical ranges. Further, the entire disclosure of the patents and publications referred in this application, if any, are hereby incorporated herein in entirety by reference.

The invention claimed is:

1. A device comprising an electrical sensor and a complex associated with a surface of the electrical sensor, wherein the complex comprises a detection probe and a label bound to the detection probe, the label being capable of absorbing radiation and separating an electrical charge upon being exposed to radiation, the label comprising a first material of a band gap Eg and a second material of band gap Eq that is smaller than Eg such that the label is configured to decouple absorbing radiation from the separating the electrical charge, and wherein the electrical sensor is capable of detecting the electrical charge.

2. The device of claim 1, wherein the electrical sensor comprises an exposed electrode surface to detect electrical perturbation, impedance, current or voltage.

3. The device of claim 1, wherein the electrical sensor comprises an electromagnetic sensor, a transistor, an electrical resistance sensor, an electrical power sensor, a magnetism sensor, an electrical current sensor, or an electrical voltage sensor.

4. The device of claim 3, wherein the FET is a metal-oxide-semiconductor FET (MOSFET), a junction FET (JFET), a metal-semiconductor FET (MESFET), or a high-electron-mobility (HEMFET).

5. The device of claim 1, wherein the electrical sensor comprises an ohmmeter, a multimeter, a galvanometer, an ammeter, a leaf electroscope, a voltmeter, a watt-hour meter, a magnetic compass, a fluxgate compass, or a magnetometer.

6. The device of claim 1, wherein the electrical sensor comprises a field effect transistor (FET).

7. The device of claim 6, wherein the FET comprises a nanowire, a nanocrystal, a nanotube, a nanopillar, a nanogap, or a patterned nanostructure.

8. The device of claim 7, wherein the FET comprises a single-walled carbon nanotube.

9. The device of claim 6, wherein the surface of the FET is functionalized.

10. The device of claim 6, wherein the surface is on the gate area of the FET.

11. The device of claim 1, wherein the complex comprises a first binding partner immobilized on the surface of the electrical sensor and an analyte bound to the first binding partner, and wherein the label is bound to the analyte.

12. The device of claim 11, wherein the analyte comprises a biomolecule.

13. The device of claim 12, wherein the analyte comprises an antigen, an antibody, a protein, a peptide, a virus, a bacterium, a carbohydrate, a lipid, a polynucleotide, a nucleic acid or a macromolecule.

14. The device of claim 11, wherein the first binding partner comprises a biomolecule.

15. The device of claim 14, wherein the first binding partner comprises an antibody, an antigen, a receptor, a ligand, a protein, a peptide, a virus, a bacterium, a carbohydrate, a lipid, a polynucleotide, a nucleic acid or a macromolecule.

16. The device of claim 11, wherein the analyte comprises an antigen and the first binding partner comprises an antibody to the antigen.

17. The device of claim 11, wherein the analyte comprises a peptide and the first binding partner comprises a receptor or ligand to the peptide.

18. The device of claim 11, wherein the analyte comprises a first polynucleotide and the first binding partner comprises a complementary polynucleotide of the first polynucleotide.

19. The device of claim 1, wherein the complex comprises a first binding partner immobilized on the surface of the electrical sensor, an analyte bound to the first binding partner, and a second binding partner bound to the analyte, and wherein the second binding partner comprises the detection probe.

20. The device of claim 19, wherein the analyte comprises a biomolecule.

21. The device of claim 20, wherein the analyte comprises an antigen, an antibody, a protein, a peptide, a virus, a bacterium, a carbohydrate, a lipid, a polynucleotide, a nucleic acid or a macromolecule.

22. The device of claim 19, wherein the first binding partner or the second binding partner comprises a biomolecule.

23. The device of claim 22, wherein the first binding partner and the second binding partner independently comprises an antibody, an antigen, a receptor, a ligand, a protein, a peptide, a virus, a bacterium, a carbohydrate, a lipid, a polynucleotide, a nucleic acid or a macromolecule.

24. The device of claim 19, wherein the analyte comprises an antigen and the first and second binding partners independently comprise an antibody to the antigen.

25. The device of claim 19, wherein the analyte comprises a peptide and the first and second partners independently comprise a receptor or ligand to the peptide.

26. The device of claim 19, wherein the analyte comprises a first polynucleotide and the first and second binding partners independently comprise a complementary polynucleotide of the first polynucleotide.

27. The device of claim 1, wherein the label comprises a quantum dot, a quantum well, a semiconductor nanoparticle, a composite-organic-inorganic nano-cluster, or a combination thereof.

28. The device of claim 1, wherein the electrical charge comprises an electrical perturbation, impedance, current, voltage, or a photo-induced charge separation.

29. The device of claim 1, wherein the radiation is electromagnetic radiation.

30. The device of claim 29, wherein the radiation is electromagnetic radiation in the form of terahertz radiation, infrared, visible light, ultraviolet light, or X-rays.

31. The device of claim 1, wherein the electrical sensor is associated with a substrate.

32. The device of claim 31, wherein the substrate comprises a polymer silicon or glass.

33. The device of claim 31, wherein the substrate comprises a microarray, a macroarray, a multi-well plate, a microfluidic device, an integrated circuit, a micro-electromechanical system (MEMS) or a combination thereof.

34. The device of claim 1, further comprising a microprocessor capable of processing signals or data detected by the electrical sensor.

35. The device of claim 1, wherein the first and second materials comprise semiconductors.

36. The device of claim 1, wherein the label further comprises a conductive material.

37. The device of claim 36, wherein the conductor is a conductive polymer.

38. A device comprising an array of electrical sensors and a complex associated with a surface of each of at least a portion of the electrical sensors, wherein each said complex comprises a detection probe and a label bound to the detection probe, said label being capable of absorbing radiation and separating an electrical charge upon being exposed to radiation, the label comprising a first material of a band gap Eg and a second material of band gap Eq that is smaller than Eg such that the label is configured to decouple absorbing radiation from the separating the electrical charge, and wherein the associated electrical sensor is capable of detecting the electrical charge.

39. The device of claim 38, wherein at least a portion of the electrical sensors are field effect transistors (FETs).

40. The device of claim 38, wherein at least a portion of the electrical sensors are individually addressable.

41. The device of claim 38, wherein each of at least a portion of the electrical sensors is associated with one or more complexes.

42. The device of claim 38, wherein a single complex is associated with two or more of the electrical sensors.

43. The device of claim 38, wherein the complexes associated with a single electrical sensor comprise the same analyte.

44. The device of claim 38, wherein at least two of the complexes associated with a signal electrical sensor comprises different analytes.

45. The device of claim 38, wherein the complexes associated with at least two of the electrical sensors comprise the same analyte.

46. The device of claim 38, wherein the complexes associated with at least two of the electrical sensors comprises different analytes.

47. The device of claim 38, wherein each of at least a portion of the electrical sensors is associated with a single complex.

* * * * *